United States Patent [19]

Lawson

[11] 4,073,619

[45] Feb. 14, 1978

[54] SAMPLING GAS FOR ANALYSIS

[75] Inventor: Robert Lawson, Middlesbrough, England

[73] Assignee: British Steel Corporation, London, England

[21] Appl. No.: 780,499

[22] Filed: Mar. 23, 1977

Related U.S. Application Data

[63] Continuation of Ser. No. 626,045, Oct. 28, 1975, abandoned.

[30] Foreign Application Priority Data

Oct. 28, 1974  United Kingdom ............... 46432/74

[51] Int. Cl.² ............................................. G01N 1/22
[52] U.S. Cl. ............................... 23/232 R; 23/254 R; 73/421.5 R
[58] Field of Search .......... 23/253 R, 253 PC, 254 R, 23/232 R, 255 R, 230 PC; 73/23, 421.5 R

[56] References Cited

U.S. PATENT DOCUMENTS

| 3,181,343 | 5/1965 | Fillon | 73/23 X |
|---|---|---|---|
| 3,329,495 | 7/1967 | Ohta et al. | 73/23 X |
| 3,432,288 | 3/1969 | Ardito et al. | 23/253 R |
| 3,463,631 | 8/1969 | Vayssiere et al. | 23/253 R |
| 3,489,518 | 1/1970 | Revell et al. | 23/253 R X |
| 3,520,657 | 7/1970 | Frumerman | 23/253 X |
| 3,528,800 | 9/1970 | Blum et al. | 23/253 X |

Primary Examiner—R.E. Serwin
Attorney, Agent, or Firm—Bacon & Thomas

[57] ABSTRACT

Gas is transferred for analysis from a sampling probe (15), which may be in the waste gas duct (14) of a steelmaking vessel (10), to remote analysers (31, 32, 33). A high transfer speed is achieved by passing the gas at a relatively high gas transfer rate from the sampling probe (15) along a relatively long first sampling duct (16), while a relatively short duct (25) takes gas at a relatively low gas transfer rate from the long duct to the analysers.

12 Claims, 1 Drawing Figure

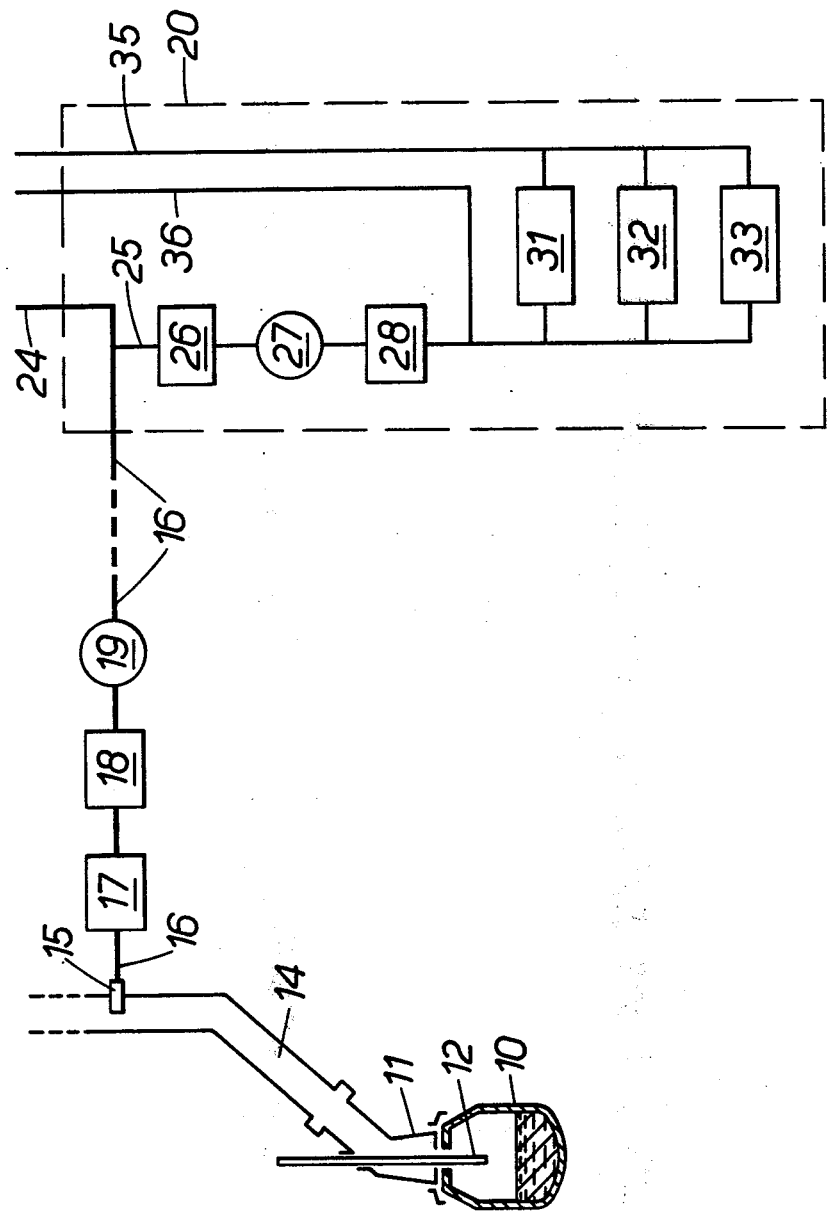

SAMPLING GAS FOR ANALYSIS

This is a continuation of application Ser. No. 626,045, filed Oct. 28, 1975, now abandoned.

This invention relates to sampling gas for analysis. It is particularly concerned with taking a sample of a gas which requires continuous monitoring by analysis and transferring the sample rapidly to analysers which are remote from the gas sampling point.

In many processes involving chemical change and giving rise to waste or exhaust gases, the chemical composition of the exhaust gases provides a useful indication of the progress of the reactions taking place in the process. One such process is the conversion of iron into steel by lancing it with oxygen, in which the decarburisation reactions which occur during the conversion can be monitored by analysing the evolved gases for oxygen, carbon monoxide and carbon dioxide.

In such a system the degree of control which can be exercised over the process is in part dependent upon the speed with which information about a process event can be extracted and made available to the controller. One factor which affects the speed of response is the time taken for the sampled gas to reach the gas analysers.

In the BOS process evolved gases and fume are collected in a hood over the steelmaking vessel at a temperature of the order of 1500° C. These process gases are ducted away to be cleaned, cooled and discharged. In order to provide good accessibility and the controlled and stable environment which the gas analysers require it is convenient to site the analysers well away from the steelmaking vessel and its exhaust system. However, a gas analyser may typically require a gas supply rate of about 1 liter per minute, and this implies a long transfer time and a correspondingly long time for the analyser to respond to a process event.

In accordance with the present invention there is provided a method for sampling and transferring gas for analysis from a source of the gas to a gas analyser remote from the gas source, in which a relatively high gas transfer rate is achieved from the gas source along a relatively long first gas sampling duct into communication with a relatively short second gas sampling duct, and a relatively low gas transfer rate is achieved from the first gas sampling duct along the second gas sampling duct and thence to the gas analyser.

The invention also provides a system for analysing a sample of gas from a gas source, in which a relatively long first gas sampling duct is adapted to transfer at a relatively high rate a gas sample from the source to a relatively short second gas sampling duct, and the second gas sampling duct is adapted to transfer part of the gas sample at a relatively low rate from the first gas sampling duct and to a gas analyser.

The excess gas not passed along the second duct is exhausted as convenient, for example to atmosphere. It is possible that the quantity of gas passed along the second duct may be more than is required by the analyser, in which case the excess can likewise be exhausted, preferably from a point close to the analyser.

One embodiment of the invention is shown by way of example in the accompanying drawing, which shows schematically and not to scale a BOS vessel with its exhaust system, an exhaust gas sampling line and analysing equipment.

The steelmaking vessel 10 is shown with a hood 11 and an oxygen lance 12. The hood draws the hot exhaust gases into a waste gas duct 14, through which they are removed from the process.

A sampling probe 15 is set into the waste gas duct wall at a point which is close to the vessel, to reduce gas transit time, but at which adequate mixing of the waste gases is assured. This point might be about 25 meters above the hood 11, and the gas temperature will have fallen to about 1300° C.

Waste gas sampled through the probe 15 passes at a rate of about 130 liters per minute along a first sampling duct 16 through a filter 17 and a cooler 18 to a vacuum pump 19. In the filter fume particles are removed, and in the cooler the gas temperature is reduced to normal ambient temperature. Beyond the pump 19 the sampled gas continues along the duct 16 at a positive pressure until the duct leads into an analysis room 20 some distance from the sampling point. The duct 16 passes through the analysis room and the bulk of the sampled gas is exhausted to atmosphere at 24. No restriction is included in the exhaust line beyond the analysis room which might create back pressure and thereby increase gas transport time.

A second sampling duct 25 branches from the first duct 16 within the analysis room and part of the sampled gas is drawn along the second duct 25 and through a further filter 26 at a rate of about 5 liters per minute by a pump 27. From the pump 27 the second sampling duct leads through a further cooler 28, to remove any residual moisture in the gas, to three gas analysers constituted by a paramagnetic oxygen analyser 31 and infrared analysers 32 and 33 for carbon monoxide and carbon dioxide respectively. From these analysers the gas is exhausted through a duct 35.

The analysers 31, 32 and 33 each require a gas supply rate of about 1 liter per minute. A bleed line 36 is therefore provided in the second gas sampling duct 25 immediately prior to the analysers to vent the excess gas to the atmosphere.

It has been found possible to operate the steelmaking process with a time lag of as little as 10 to 15 seconds between sampling the waste gas and obtaining an analysis of its oxygen, carbon monoxide and carbon dioxide content by the utilisation of this invention.

The pump 19 transfers gas at about 56 liters per minute along the duct 16 at a pressure of about 22 mm mercury gauge, pressures between 5 or 10 and 50 mm mercury gauge being considered generally suitable. The duct 16 is unrestricted and of 12.7 mm internal diameter.

The second gas sampling duct 25 is of 6.3 mm internal diameter and is provided with gas from the pump 27 at a pressure of approximately 60 mm mercury gauge.

The whole sampling and analysis system is operated under positive pressure at all times.

We claim:

1. A method for the rapid transfer of gas from a sampling probe at a gas source to a gas analyser remote from the gas source to thereby decrease the time interval between sampling and analysis, comprising passing the gas from the probe along a first gas sampling duct intercommunicating at a junction with a second gas sampling duct which transfers the gas sample to the gas analyser; the first gas sampling duct being relatively long compared with the second gas sampling duct and exhausting to the atmosphere after said junction; and second sampling duct having a bleed line just prior to said analyser to exhaust under pressure a proportion of the gas in the second duct to the atmosphere; the gas being transferred along the first duct at a high gas transfer rate relative to the transfer rate along the second duct.

2. A method according to claim 1 wherein the gas is mixed waste gas from a basic oxygen steelmaking process.

3. A method according to claim 1 wherein the relatively low gas transfer rate is between 5 and 25% of the relatively high gas transfer rate.

4. A method according to claim 1 wherein the gas is passed along the sampling ducts at a pressure greater than atmospheric pressure.

5. A method according to claim 4 wherein the pressure is between 5 and 50 mm mercury gauge.

6. A system for the rapid transfer of gas from a sampling probe at a gas source to a gas analyser remote from the gas source to thereby decrease the time interval between sampling and analysis, comprising a first gas sampling duct connecting to the sampling probe and extending to the vicinity of the gas analyser and a second gas sampling duct intercommunicating with the first gas sampling duct at a junction and providing a passage for flow of a sample of gas from the first gas sampling duct to the gas analyser, said first sampling duct having means to exhaust said gas to the atmosphere after said junction, and being relatively long compared with said second sampling duct and being adapted to transfer gas at a high gas transfer rate as compared with the gas transfer rate in the second sampling duct; said second sampling duct having means to bleed a proportion of the gas sample under pressure to the atmosphere prior to the gas sample entering the analyser.

7. A system according to claim 6 wherein the sampling probe is situated in the waste gas duct of a basic oxygen steel-making vessel.

8. A system according to claim 6 wherein the first and/or the second gas sampling duct is provided with a filter and a pump.

9. A system according to claim 6 wherein the first gas sampling duct has approximately four times the cross-sectional area of the second gas sampling duct.

10. A system according to claim 8, wherein the first and second sampling ducts each contain a pump.

11. A system according to claim 8, wherein means for filtering the sample gas is present in said first sampling duct to filter said gas sample prior to entry of said gas sample into a pump in said first sample duct and cooling means in said second sampling duct prior to said bleeding means.

12. A system according to claim 6 wherein the second gas sampling duct exhaust to atmosphere beyond its connection with the gas analyser.

* * * * *